(12) United States Patent
Kim et al.

(10) Patent No.: US 11,154,636 B2
(45) Date of Patent: Oct. 26, 2021

(54) ANTIMICROBIAL BIOPOLYMER COMPOSITIONS, METHODS OF SYNTHESIS, AND APPLICATIONS OF USE

(71) Applicant: ARIZONA BOARD OF REGENTS ON BEHALF OF THE UNIVERSITY OF ARIZONA, Tucson, AZ (US)

(72) Inventors: Minkyu Kim, Tucson, AZ (US); Christopher P. Camp, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 61 days.

(21) Appl. No.: 16/253,825

(22) Filed: Jan. 22, 2019

(65) Prior Publication Data

US 2019/0224362 A1  Jul. 25, 2019

Related U.S. Application Data

(60) Provisional application No. 62/619,430, filed on Jan. 19, 2018.

(51) Int. Cl.
| | |
|---|---|
| *A61L 15/32* | (2006.01) |
| *C07K 14/78* | (2006.01) |
| *C08J 3/075* | (2006.01) |
| *C07K 14/47* | (2006.01) |
| *A61K 47/64* | (2017.01) |
| *A61L 27/22* | (2006.01) |
| *A61K 38/17* | (2006.01) |
| *A61L 15/46* | (2006.01) |

(52) U.S. Cl.
CPC .......... *A61L 15/32* (2013.01); *A61K 47/6435* (2017.08); *A61L 15/46* (2013.01); *A61L 27/227* (2013.01); *C07K 14/4723* (2013.01); *C07K 14/78* (2013.01); *C08J 3/075* (2013.01); *A61K 38/1719* (2013.01); *A61K 38/1751* (2013.01); *A61L 2300/252* (2013.01); *A61L 2300/404* (2013.01); *C07K 2319/00* (2013.01); *C07K 2319/21* (2013.01); *C07K 2319/22* (2013.01)

(58) Field of Classification Search
None
See application file for complete search history.

(56) References Cited

PUBLICATIONS

Sousa et al. "Production of a polar fish antimicrobial peptide in *Escherichia coli* using an ELP-intein tag" J. Biotechnology 234:83-89. (Year: 2016).*

Hu et al. "Expression and Purification of an Antimicrobial Peptide by Fusion with Elastin-like Polypeptides in *Escherichia coli*" Appl. Biochem. Biotechnol. 160:2377-2387. (Year: 2010).*

* cited by examiner

*Primary Examiner* — Sudhakar Katakam
*Assistant Examiner* — Zachary J Miknis
(74) *Attorney, Agent, or Firm* — Nguyen Tarbet LLC

(57) ABSTRACT

Biopolymer compositions comprising antimicrobial peptides (AMPs) for treating infections such as bacterial infections, viral infections, fungal infections, and parasitic infections. The compositions herein may also be used for treating infections associated with antibiotic-resistant bacteria, antifungal-resistant fungi, antiviral-resistant viruses, or for treating biological warfare agents (BWAs) such as *Bacillus anthracis* and *Yersenia pestis*. The present invention also provides methods of synthesis of said biopolymer compositions, wherein AMP biopolymers can be synthesized as an artificially engineered protein by genetically fusing an AMP; a protein that behaves similarly to polymer tethers; and a protein as a modifiable material platform that can transform to self-assembled nanoparticles, self-standing films, or adhesives to easily attach tethered AMPs onto any biomaterial surface for various clinical applications.

9 Claims, 2 Drawing Sheets
(2 of 2 Drawing Sheet(s) Filed in Color)
Specification includes a Sequence Listing.

SEQUENCE LISTING

<160> NUMBER OF SEQ ID NOS: 6

<210> SEQ ID NO 1

```
<211> LENGTH: 5
<212> TYPE: PRT
<213> ORGANISM: Artificial Sequence
<220> FEATURE:
<223> OTHER INFORMATION: Peptide fragment for synthetic elastin-like
      polypeptide (ELP)
<220> FEATURE:
<221> NAME/KEY: misc_feature
<222> LOCATION: (4)..(4)
<223> OTHER INFORMATION: Xaa can be any naturally occurring amino acid

<400> SEQUENCE: 1

Val Pro Gly Xaa Gly
1               5

<210> SEQ ID NO 2
<211> LENGTH: 5
<212> TYPE: PRT
<213> ORGANISM: Artificial Sequence
<220> FEATURE:
<223> OTHER INFORMATION: Peptide fragment for synthetic elastin-like
      polypeptide (ELP)

<400> SEQUENCE: 2

Val Pro Gly Tyr Gly
1               5

<210> SEQ ID NO 3
<211> LENGTH: 5
<212> TYPE: PRT
<213> ORGANISM: Artificial Sequence
<220> FEATURE:
<223> OTHER INFORMATION: Peptide fragment for synthetic elastin-like
      polypeptide (ELP)

<400> SEQUENCE: 3

Val Pro Gly Ala Gly
1               5

<210> SEQ ID NO 4
<211> LENGTH: 5
<212> TYPE: PRT
<213> ORGANISM: Artificial Sequence
<220> FEATURE:
<223> OTHER INFORMATION: Peptide fragment for synthetic elastin-like
      polypeptide (ELP)

<400> SEQUENCE: 4

Val Pro Gly Ser Gly
1               5

<210> SEQ ID NO 5
<211> LENGTH: 9
<212> TYPE: PRT
<213> ORGANISM: Artificial Sequence
<220> FEATURE:
<223> OTHER INFORMATION: Hydrophilic polymer-like protein for protein
      tether

<400> SEQUENCE: 5

Ala Gly Ala Gly Ala Gly Pro Glu Gly
1               5

<210> SEQ ID NO 6
<211> LENGTH: 37
<212> TYPE: PRT
<213> ORGANISM: Artificial Sequence
<220> FEATURE:
<223> OTHER INFORMATION: Antimicrobial peptide LL37
```

```
<400> SEQUENCE: 6

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
            35
```

ANTIMICROBIAL BIOPOLYMER COMPOSITIONS, METHODS OF SYNTHESIS, AND APPLICATIONS OF USE

CROSS-REFERENCES TO RELATED APPLICATIONS

This application a non-provisional and claims benefit of U.S. Patent Application No. 62/619,430 filed Jan. 19, 2018, the specification of which is incorporated herein in its entirety by reference.

REFERENCE TO A SEQUENCE LISTING

Applicant asserts that the paper copy of the Sequence Listing is identical to the Sequence Listing in computer readable form found on the accompanying computer file, entitled >>>UNIA_17_44_NP_ST25.txt<<<. The content of the sequence listing is incorporated herein by reference in its entirety.

FIELD OF THE INVENTION

The present invention relates to biopolymers, more particularly to biopolymers comprising tethered antimicrobial peptides (AMPs) for treating microbial infections.

BACKGROUND OF THE INVENTION

Tethering antimicrobial peptides (AMPs) to a biomaterial surface is a promising therapeutic to treat a broad range of microbial infections (e.g., by enhancing AMP stability, prolonging AMP activity in vivo, reducing AMP dosage, reducing AMP toxicity, etc.), including antimicrobial-resistant microorganisms. However, complex chemical synthesis of conventional AMP-incorporated materials limits the use of antimicrobial materials in clinical settings. Furthermore, the complex chemical synthesis and processing of conventional AMP-incorporated materials is impractical for many AMPs due to high cost burdens. For example, conventional AMP-incorporated materials are comprised of: an AMP; a long, flexible, hydrophilic polymer tether; and a biomaterial that is specific to the clinical application. Each component is synthesized individually and subsequently connected in additional steps.

AMP biopolymers can be synthesized as an artificially engineered protein (an "all-in-one" artificial protein) by genetically fusing (1) an AMP; (2) a protein that behaves similarly to polymer tethers; and (3) a protein as a modifiable material platform that can transform to self-standing nanoparticles and films, or adhesives to easily attach tethered AMPs onto any biomaterial surface for various clinical applications. Genetic engineering allows for modification of single amino acids of the artificial protein, e.g., for modifying the AMP sequence for better potency, changing to a different AMP, improving the material properties, etc. Biosynthesis using biological hosts precisely produces the artificial proteins as designed, reducing inconsistent antimicrobial activity by eliminating complex chemical processing. In addition, because these proteins can be purified without traditional chromatography, and because biosynthesis is scalable, there is significant potential for the clinical translation of the AMP-incorporated materials using cost-effective biomanufacturing.

The development of this "all-in-one" artificial protein as a universal material platform for AMPs serves to mitigate current barriers to the efficient and cost-effective development and application of AMP-incorporated materials for their use in the clinical setting.

SUMMARY OF THE INVENTION

The present invention features biopolymers comprising antimicrobial peptides (AMPs), as well as applications of use, methods of synthesis, and compositions for synthesis. The methods and compositions herein help to simplify and unify the synthesis of various AMP-incorporated materials.

The biopolymers of the present invention may be used for treating microbial infections, including bacterial infections, fungal infections, parasitic infections, viral infections, infections associated with antibiotic-resistant bacteria or antifungal-resistant fungi or antiviral-resistant viruses, biological warfare agents (BWAs) such as *Bacillus anthracis* and *Yersenia pestis*, etc. The biopolymers of the present invention may be used to kill or reduce the growth of the particular microbe (e.g., bacteria, fungus, parasite, virus, etc.).

The ELP(Tyr) design provided herein produces AMP antimicrobial agents in the form of nanoparticles, films/membranes, and strong adhesives to biomaterial surfaces. Elastin-like polypeptide (ELP)-fusion proteins self-assemble into multiple material structures in physiological conditions as a function of: (i) the designed phase transition temperature ($T_t$); (ii) molar mass ratio between the ELP and fused proteins; and (iii) concentration of ELP-fusion protein in solution. This helps guide the development of AMP nanoparticles.

The present invention provides antimicrobial material (AMP)-biopolymer compositions comprising an elastin-like polypeptide (ELP); an antimicrobial material (AMP); and a protein (polypeptide, e.g., with antifouling characteristics) tether connecting the ELP and the AMP. In certain embodiments, the ELP comprises at least one tyrosine residue (e.g., ELP(Tyr)). In certain embodiments, the ELP, e.g., ELP(Tyr), is according to the formula $(VPGXaaG)_m$ (SEQ ID NO: 1). In certain embodiments, the ELP, e.g., ELP(Tyr), is according to the formula $[(VPGXaaG)_j(VPGYG)_k(VPGXaaG)_l]_n$ (note VPGYG is SEQ ID NO: 2), thus the formula may be written $[(SEQ\ ID\ NO:\ 1)_j(SEQ\ ID\ NO:\ 2)_k(SEQ\ ID\ NO:\ 1)_l]_n$. In certain embodiments, Xaa is a polar amino acid, a non-polar amino acid, a charged amino acid, or a combination thereof, not including proline. For example, in certain embodiments, Xaa is alanine. In some embodiments, Xaa is serine. In some embodiments, Xaa is glycine. In some embodiments, Xaa is arginine. In some embodiments, Xaa is asparagine. In some embodiments, Xaa is aspartic acid. In some embodiments, Xaa is cysteine. In some embodiments, Xaa is glutamine. In some embodiments, Xaa is glutamic acid. In some embodiments, Xaa is histidine. In some embodiments, Xaa is isoleucine. In some embodiments, Xaa is leucine. In some embodiments, Xaa is lysine. In some embodiments, Xaa is methionine. In some embodiments, Xaa is phenylalanine. In some embodiments, Xaa is threonine. In some embodiments, Xaa is tryptophan. In some embodiments, Xaa is tyrosine. In some embodiments, Xaa is valine. In some embodiments, Xaa may be one or a combination of the aforementioned examples of amino acids. A composition may comprise a plurality of ELPs with one or different formulas.

The present invention also features antimicrobial material (AMP)-biopolymer compositions comprising: an elastin-like polypeptide (ELP); an antimicrobial material (AMP); and a peptide tether connecting the ELP and the AMP, wherein the peptide tether connects to the AMP at the AMP's N-terminus or C-terminus. In some embodiments, the ELP comprises at least one tyrosine residue.

The ELP may be according to the formula [(VPGXaaG, SEQ ID NO: 1)$_j$(VPGYG, SEQ ID NO: 2)$_k$(VPGXaaG, SEQ ID NO: 1)$_l$]$_n$. In some embodiments, Xaa is alanine, serine, arginine, asparagine, aspartic acid, cysteine, glutamine, glutamic acid, glycine, histidine, isoleucine, leucine, lysine, methionine, phenylalanine, threonine, tryptophan, tyrosine, or valine.

In some embodiments, the protein tether comprises [VPGSG]$_i$ (SEQ ID NO: 4) or [AGAGAGPEG]$_n$ (SEQ ID NO: 5). In some embodiments, the composition self-assembles into nanoparticles. In some embodiments, tyrosine residues are cross-linked to form a self-standing film or membrane material.

In some embodiments, the tyrosine residue allows the composition to adhere to a surface after hydroxylation by tyrosinase. In some embodiments, the surface is a cloth, a plastic, a glass, a metal, or a combination thereof. In some embodiments, the surface is a medical device, a dressing, a clothing, or a combination thereof. In some embodiments, the peptide tether has anti-fouling characteristics. In some embodiments, the composition is for killing an infectious agent or for reducing growth of an infectious agent. In some embodiments, the infectious agent is a bacteria, a virus, a fungus, or a parasite.

In certain embodiments, the AMP is selected from the group consisting of LL37, RL37, Dermcidin, Protegrin, etc. or a combination thereof. However, the present invention is not limited to the aforementioned AMPs.

In certain embodiments, the AMP biopolymer composition self-assembles into nanoparticles. In certain embodiments, the tyrosine residues are cross-linked (e.g., by photo-crosslinking using a photoinitiator, e.g., riboflavin (vitamin B2), Tris(2,2-bipyridine)ruthenium(II), etc., to form a self-standing film or membrane material.

The tyrosine residue(s) of the composition allow the composition to adhere to a surface (e.g., cloth, plastic, metal, glass, a combination thereof; e.g., a medical device such as an endoscope or an implant, a dressing, a clothing, or a combination thereof), e.g., after hydroxylation by tyrosinase.

In certain embodiments, AMP is connected to the tether by its N-terminus. In certain embodiments, the AMP is connected to the tether by its C-terminus. In certain embodiments, the composition comprises an AMP molecule connected to the tether at its N-terminus and an AMP molecule connected to the tether at its C-terminus. For example, in certain embodiments, the composition is ELP(Tyr)-tether-AMP. In certain embodiments, the composition is AMP-tether-ELP(Tyr). In certain embodiments, the composition is ELP-tether-AMP. In certain embodiments, the composition is AMP-tether-ELP. In certain embodiments, the composition comprises a mix of different compositions, e.g., a mix of AMP-tether-ELP and ELP-tether-AMP.

In certain embodiments, the composition is for treating an infection, e.g., a bacterial infection, a viral infection, a fungal infection, or a parasitic infection. In certain embodiments, the infection is caused by a biological warfare agent. In certain embodiments, the infection is caused by an antimicrobial resistant microorganism. In certain embodiments, the composition is for killing an infectious agent or for reducing growth of an infectious agent.

The present invention also provides films comprising an antimicrobial material (AMP)-biopolymer according to the present invention as described herein. For example, the AMP-biopolymer may comprise an elastin-like polypeptide (ELP) (e.g., ELP(Tyr)); an antimicrobial material (AMP); and a protein tether connecting the ELP and the AMP. In some embodiments, the AMP-biopolymer comprises: an elastin-like polypeptide ELP(Tyr) according to the formula [(VPGXaaG, SEQ ID NO: 1)$_j$(VPGYG, SEQ ID NO: 2)$_k$ (VPGXaaG, SEQ ID NO: 1)$_l$]$_n$; an antimicrobial peptide (AMP); and a peptide tether connecting the ELP and the AMP. The peptide tether connects to the AMP at the AMP's N-terminus or C-terminus. The ELP may be cross-linked to form the film material. For example, the tyrosines in the ELP(Tyr) may be cross-linked to form a film.

In some embodiments, Xaa is alanine, serine, arginine, asparagine, aspartic acid, cysteine, glutamine, glutamic acid, glycine, histidine, isoleucine, leucine, lysine, methionine, phenylalanine, threonine, tryptophan, tyrosine, or valine. In some embodiments, the AMP is selected from the group consisting of LL37, RL37, Dermcidin, Protegrin, or a combination thereof. However, the present invention is not limited to the aforementioned AMPs. In some embodiments, the protein tether comprises [VPGSG]$_i$ (SEQ ID NO: 4) or [AGAGAGPEG]$_n$ (SEQ ID NO: 5).

The present invention also provides therapeutic cocktail compositions comprising two or more different antimicrobial (AMP)-biopolymer compositions according to the present invention. For example, in some embodiments, each AMP biopolymer composition comprises an elastin-like polypeptide ELP(Tyr) according to the formula [(VPGXaaG, SEQ ID NO: 1)$_j$(VPGYG, SEQ ID NO: 2)$_k$ (VPGXaaG, SEQ ID NO: 1)$_k$]$_n$; an antimicrobial peptide (AMP); and a peptide tether connecting the ELP and the AMP. The peptide tether may connect to the AMP at the AMP's N-terminus or C-terminus. In some embodiments, the AMP is selected from the group consisting of LL37, RL37, Dermcidin, Protegrin, or a combination thereof. However, the AMP is not limited to the aforementioned examples of AMPs.

The present invention also provides designed nucleic acid sequences encoding AMP-biopolymer compositions according to the present invention. The present invention also features isolated nucleic acid sequences encoding AMP-biopolymer compositions according to the present invention. The present invention also provides amino acid sequences of AMP-biopolymer compositions according to the present invention.

The present invention also provides methods of synthesizing AMP-biopolymer compositions according to the present invention. In certain embodiments, the method comprises introducing (to a host for gene expression such as but not limited to a bacterial host) a vector encoding the AMP-biopolymer composition; expressing the AMP-biopolymer composition; and purifying the AMP-biopolymer composition. In certain embodiments, the gene expression host is a bacterial host, e.g., *Escherichia coli*. The gene expression host is not limited to *E. coli*. In certain embodiments, purifying the AMP biopolymer composition comprises an inverse transition cycling (ITC) method.

The present invention also provides methods for purifying AMP biopolymer compositions according to the present invention, wherein the method comprises an inverse transition cycling (ITC) method.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

This patent application contains at least one drawing executed in color. Copies of this patent or patent application publication with color drawing(s) will be provided by the Office upon request and payment of the necessary fee.

The features and advantages of the present invention will become apparent from a consideration of the following detailed descriptions presented in connection with the accompanying drawings in which.

DETAILED DESCRIPTION OF THE INVENTION

The present invention features biopolymers comprising antimicrobial peptides (AMPs), as well as applications of use, methods of synthesis, and compositions for synthesis. The present invention provides compositions (e.g., a material platform) that stabilize AMPs and helps improve the ability to use AMPs as therapeutic agents for treating infections, e.g., bacterial infections, fungal infections, parasitic infections, viral infections, infections associated with antibiotic-resistant bacteria or antifungal-resistant fungi or antiviral-resistant viruses, biological warfare agents (BWAs) such as *Bacillus anthracis* and *Yersenia pestis*, etc. The biopolymers of the present invention may be used to kill or reduce the growth of the particular microbe or infectious agent (e.g., bacteria, fungus, parasite, virus, etc.).

The present invention discloses AMP-biopolymer compositions and methods for synthesizing the AMP-biopolymer compositions by integrating the synthesis of the AMP, the tether, and a biomaterial. To enable this approach, the biomaterial (platform, scaffold) may need to be able to transform into self-assembled nanoparticles, into adhesives to form a coating, and/or cross-link to form a film, gel, filter, antimicrobial clothing material, etc. The biopolymer may also need to contain a region that behaves structurally and physically similar to polymer tethers for enhanced AMP activity and stability.

Figure 1:
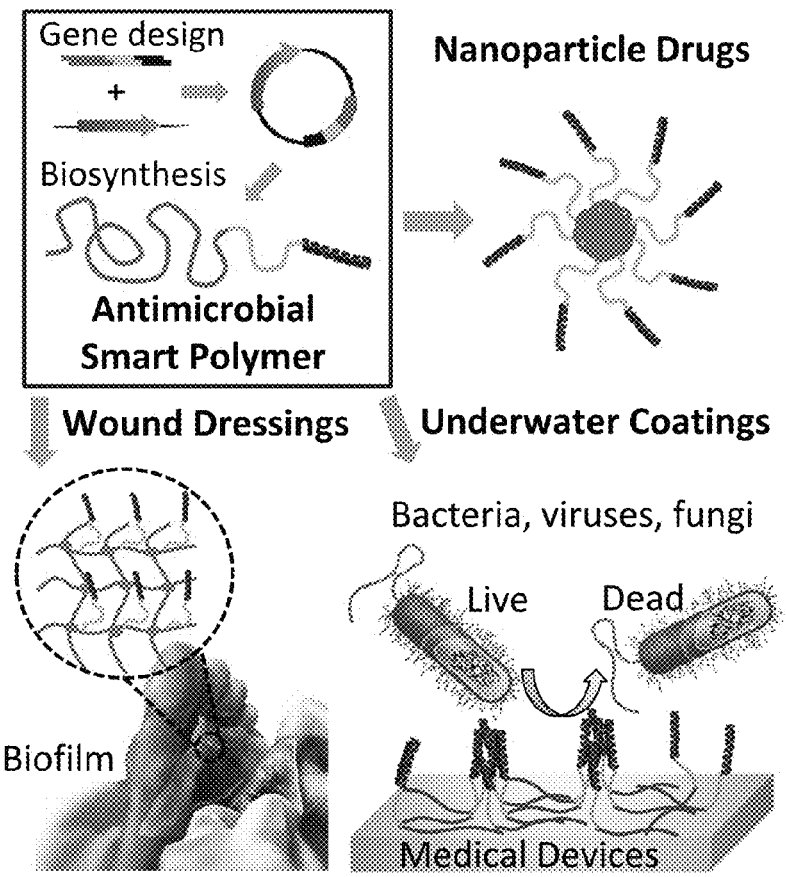
FIG. 1 shows a schematic view of the synthesis of AMP biopolymers (e.g., ELPs) of the present invention as well as applications thereof.

The AMP biopolymer compositions (e.g., platforms, scaffolds) feature (1) a biocompatible scaffold (e.g., elastin-like polypeptide (ELP), resilin-like polypeptide (RLP), etc.); (2) a tether, and an AMP. Without wishing to limit the present invention to any theory or mechanism, it is believed that the ELP platform is advantageous because of its tractability to transform into many types of biomaterials: (i) biocompatible ELP self-assembles into nanoparticles when heated above its phase-transitioning temperature ($T_t$), (ii) covalently bonded Tyr residues can form a self-standing film or membrane, and (iii) Tyr hydroxylation allows Tyr-containing materials to strongly adhere to surfaces. FIG. 1 illustrates the overall strategy of the compositions (e.g., ELPs) herein, wherein AMP biopolymers can be designed and synthesized as a single unit. A gene is designed to yield a particular ELP (e.g., ELP(Tyr)) linked to a tether linked to an AMP, wherein the whole unit is called the biopolymer. Because the biopolymer is designed at the genetic level, modification of the components can be made by altering the nucleic acid sequence that encodes the biopolymer through genetic engineering. The biopolymer can self-assemble, e.g., to create a nanoparticle drug. In some embodiments, the tyrosine residues are utilized for photo-crosslinking or for attaching to surfaces such as but not limited to medical device surfaces or clothing, or for creating a biofilm for applications such as wound dressings.

Elastin-Like Polypeptide (ELP) Scaffold

The scaffold component of the AMP biopolymer compositions may comprise an elastin-like polypeptide (ELP). ELPs comprise pentapeptide repeats (VPGXaaG)m (SEQ ID NO: 1), wherein Xaa is one or a plurality of amino acids (not including proline) (e.g., polar amino acids, non-polar amino acids, charged amino acids, or a combination thereof). In some embodiments, the ELP comprises the formula ELP$(X_jY_kX_l)_n$, wherein X is SEQ ID NO: 1 (VPGXaaG), and Y is SEQ ID NO: 2 (VPGYG). Thus, the ELP may comprise the formula [(VPGXaaG)$_j$(VPGYG)$_k$ (VPGXaaG)$_l]_n$, e.g., [(SEQ ID NO: 1)$_j$(SEQ ID NO: 2)$_k$ (SEQ ID NO: 1)$_l]_n$. For example, in some embodiments, Xaa is alanine and the formula is ELP$(A_jY_kA_l)_n$, which=[(VPGAG)$_j$(VPGYG)$_k$(VPGAG)$_l]_n$ (wherein VPGAG is SEQ ID NO: 3). In some embodiments, Xaa is serine and the formula is ELP$(S_jY_kS_l)_n$, which=[(VPGSG)$_j$(VPGYG)$_k$(VPGSG)$_l]_n$ (wherein VPGSG is SEQ ID NO: 4). Xaa is not limited to serine or alanine. In some embodiments, Xaa is glycine (and the formula is ELP$(G_jY_kG_l)_n$). In some embodiments, Xaa is arginine (and the formula is ELP$(R_jY_kR_l)_n$). In some embodiments, Xaa is asparagine (and the formula is ELP $(N_jY_kN_l)_n$). In some embodiments, Xaa is aspartic acid and the formula is ELP$(D_jY_kD_l)_n$). In some embodiments, Xaa is cysteine (and the formula is ELP$(C_jY_kC_l)_n$). In some embodiments, Xaa is glutamine (and the formula is ELP $(Q_jY_kQ_l)_n$). In some embodiments, Xaa is glutamic acid (and the formula is ELP$(E_jY_kE_l)_n$). In some embodiments, Xaa is histidine (and the formula is ELP$(H_jY_kH_l)_n$). In some embodiments, Xaa is isoleucine (and the formula is ELP $(I_jY_kI_l)_n$). In some embodiments, Xaa is leucine (and the formula is ELP$(L_jY_kL_l)_n$). In some embodiments, Xaa is lysine (and the formula is ELP$(K_jY_kK_l)_n$). In some embodiments, Xaa is methionine (and the formula is ELP$(M_jY_k M_l)_n$). In some embodiments, Xaa is phenylalanine (and the formula is ELP$(F_jY_kF_l)_n$). In some embodiments, Xaa is threonine (and the formula is ELP$(T_jY_kT_l)_n$). In some embodiments, Xaa is tryptophan (and the formula is ELP $(W_jY_kW_l)_n$). In some embodiments, Xaa is tyrosine (and the formula is ELP$(Y_jY_kY_l)_n$). In some embodiments, Xaa is valine (and the formula is ELP$(V_jY_kV_l)_n$).

In some embodiments, j=1, 2, 3, 4, 5, 6, etc. In some embodiments, k=1, 2, 3, 4, 5, 6, etc. In some embodiments, l=1, 2, 3, 4, 5, 6, etc. In some embodiments, n=1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, more than 50 etc.

Without wishing to limit the present invention to any theory or mechanism, n may be determined based on what works well for purification processes, e.g., n may need to be large enough for purification. However, n is not limited to any particular number. In some embodiments, n is 3 or more, 4 or more, 5 or more, etc., e.g., in some embodiments, n=4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, more than 50, etc.

In some embodiments, m is 10. In some embodiments, m is a number from 10 to 100. In some embodiments, m is a number from 100 to 200. In some embodiments, m is a number from 200 to 300. In some embodiments, m is a number from 10 to 400 or more. In some embodiments, m=3x, wherein x is a number from 1 to 100, e.g., x=1 and m=3; x=2 and m=6; x=20 and m=60; x=50 and m=150; x=60 and m=180; etc. The present invention is not limited to the aforementioned values for m.

In some embodiments, the ELP comprises tyrosine residues (ELP(Tyr)).

The $T_t$ of an ELP is adjustable by combining polar and non-polar amino acids in the non-conserved $X_{aa}$ position, and controlling the ELP molar masses. An ELP with Tyr and Ala or Tyr and Ser residues in the $X_{aa}$ position is shown in Table 1 below. Note that ELP $(A_2Y_1A_2)_{36}$=[(VPGAG)$_2$(VPGYG)$_1$(VPGAG)$_2$]$_{36}$ (Xaa is alanine). ELP $(S_2Y_1S_2)_{36}$=[(VPGSG)$_2$(VPGYG)$_1$(VPGSG)$_2$]$_{36}$ (Xaa is serine). ELP $(S_2Y_1S_1)_{45}$=[(VPGSG)$_2$(VPGYG)$_1$(VPGSG)$_1$]$_{45}$ (Xaa is serine). ELP $(A_2Y_1A_1)_{45}$ [(VPGAG)$_2$(VPGYG)$_1$(VPGAG)$_1$]$_{45}$ (Xaa is alanine).

TABLE 1

Proposed ELP(Tyr) sequences and their expected and experimental transition temperature ($T_t$)

| ELP (Tyr) | $T_{t, expected}$ | Number of ELP pentapeptide (m) | $T_{t, experimental}$ of ELP (Tyr) |
|---|---|---|---|
| ELP $(A_2Y_1A_2)_{36}$ | 25° C. | 180 | 25° C. |
| ELP $(S_2Y_1S_2)_{36}$ | 29° C. | 180 | 29° C. (expected) |
| ELP $(S_2Y_1S_1)_{45}$ | 24° C. | 180 | TBD |
| ELP $(A_2Y_1A_1)_{45}$ | 20° C. | 180 | TBD |

Expected $T_t$ ($T_{t,expected}$) and Experimental $T_t$ ($T_{t,experimental}$) are according to previous research by Ingrole, R., Tao et al. "*Synthesis and Immunogenicity Assessment of Elastin-Like Polypeptide-M2e Construct as an Influenza Antigen*" Nano Life, 2014. These results were obtained using alanine in Xaa position instead of serine, e.g. ELP $(A_2Y_1A_2)_n$ vs. ELP$(S_2Y_1S_2)_n$. The expected $T_t$ ($T_{t,expected}$) of ELP $(A_2Y_1A_2)_n$ matched the experimental $T_t$ ($T_{t,experimental}$) when the number of ELP pentapeptide repeats were 180 (n=36). The $T_t$ of the ELP can be changed when fused to AMPs but the larger ELP$(A_2Y_1A_2)_{36}$ had less change in $T_t$ when fused to a hydrophilic peptide relative to the smaller ELP$(A_2Y_1A_2)_{24}$.

The ELPs herein were designed based on ELP(Tyr) sequences with the same number of ELP pentapeptide repeats (to similarly match the $T_{t,experimental}$ of ELP(Tyr) with the $T_{t,expected}$ (see Table 1). The sequence variants facilitate: (i) $T_t$ of ELP(Tyr) between room temperature (RT) and body temperature (BT) when fused with amphiphilic AMPs; and (ii) investigation of the relationship between AMP activity and the quantity of Tyr residues, which influences the strength of the film/coating materials. LL37 is a cationic, amphiphilic, antimicrobial peptide, composed of 37 amino acids. The present invention provides a fusion of the LL37 peptide to the C-terminus of ELP(Tyr): ELP(Tyr)-LL37. LL37 can damage microbial membranes, including *E. coli* and *S. aureus*, via carpet or toroidal models. Solid-state NMR spectroscopy revealed that LL37 forms dimer or tetramer oligomer structures like the Barrel-Stave pore model when they bind to the membrane. Since LL37 covers the most-widely accepted microbe lysis mechanisms, it was chosen as a representative model of AMP lysis activity as part of the artificial protein.

Figure 2A:
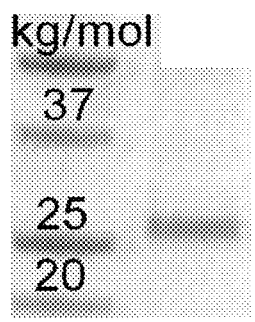
FIG. 2A shows SDS-PAGE analysis of ELP$(A_1Y_1A_1)_{24}$-LL37 purified by inverse transition cycling methods.
Figure 2B:
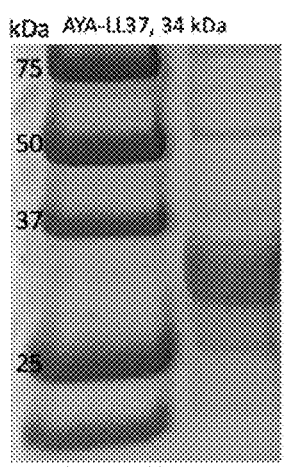
FIG. 2B shows SDS-PAGE analysis of ELP$(S_2Y_1S_2)_8$-LL37 purified by salting out methods.
Figure 2C:
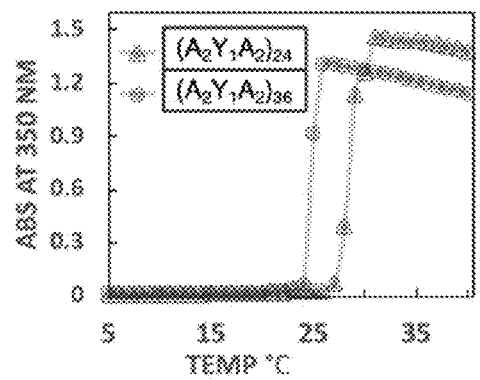
FIG. 2C shows UV/Vis spectrophotometer analysis of the phase-transitioning temperatures of ELP$(A_2Y_1A_2)_{24}$ and ELP$(A_2Y_1A_2)_{36}$, respectively.

The short ELP$(S_2Y_1S_2)_8$-LL37 gene was designed with multiple restriction enzyme sites for gene editing. The gene was cloned into a protein expression vector (see FIG. 1 for a schematic view) and was produced in *E. coli*. The $T_t$ of ELP$(S_2Y_1S_2)_8$-LL37 was too high to apply non-chromatographic $T_t$ purification (>70° C.). Its size was confirmed by metal ion affinity chromatography by attaching the affinity tag to the protein (see FIG. 3). FIG. 2A shows SDS-PAGE analysis of $(S_2Y_1S_2)_8$-LL37 purified by Ni-NTA chromatography methods. FIG. 2B shows SDS-PAGE analysis of ELP$(A_1Y_1A_1)_{24}$-LL37 purified by inverse transition cycling methods. FIG. 2C shows UV/Vis spectrophotometer analysis of the phase-transitioning temperatures of ELP$(A_2Y_1A_2)_{24}$ and ELP$(A_2Y_1A_2)_{36}$, respectively.

Figure 3:
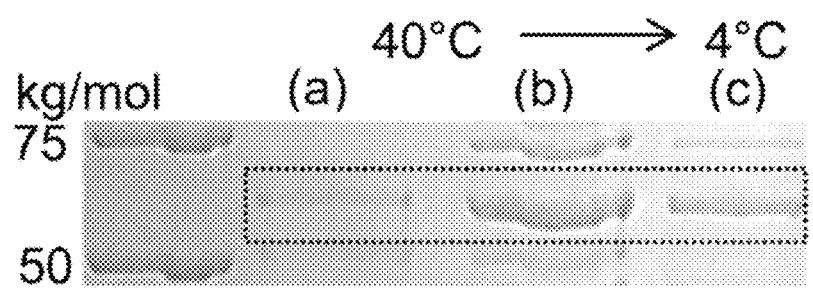
FIG. 3 shows ELP$(S_2Y_2S_2)_{16}$-LL37 with PBS containing 25 wt % ammonium sulfate. At 40° C., the protein was not in solution (a), but the protein was in precipitate (b) and dissolved (c) at 4° C.

The size of the ELP was doubled using the golden gate cloning method, and the phase transition of ELP was captured by decreasing the $T_t$ in a solution with high salt concentration (see FIG. 3). This approach did not work with the shorter ELP, indicating larger ELPs exhibit lower $T_{t,experimental}$ and more closely match $T_{t,expected}$. Without wishing to limit the present invention to any theory or mechanism, ELP(Tyr)-LL37 proteins may reach the target $T_t$ and facilitate non-chromatographic ELP-fusion protein purification by using the inverse transition cycling (ITC) method that utilizes ELP phase changes above and below its $T_t$ (see FIG. 3).

Inexpensive purification of elastin-like polypeptides (ELP), including ELP(Tyr) and biopolymers containing ELP is carried out through the Inverse Transition Cycling (ITC) method by utilizing the ELP phase change behavior, where ELP phase changes occur at its transition temperature ($T_t$). $T_t$ is determined by the polarity of amino acids in the Xaa position and quantity of pentapeptide repeats in ELP. Below its $T_t$, ELP is soluble and above its $T_t$, ELP is insoluble. The ITC method to purify an ELP mixture is carried out by first centrifuging the ELP mixture at a temperature below $T_t$ when ELP is soluble and discarding the pellet. This removes insoluble impurities when ELP is soluble. Next, the temperature of the ELP mixture is raised above $T_t$ causing ELPs display increased hydrophobic behavior, aggregate and collapse from solution. The ELP mixture is then centrifuged, and the soluble portion is removed. This removes soluble impurities when ELP is insoluble. Repeating this process several times yields highly pure ELP as many impurities cannot reversibly precipitate and dissolve in solutions. To capture target proteins, chromatography often requires expensive columns as in ion-exchange or size exclusion, or peptide tags (e.g. His-Tag, Strep-Tag, etc.) on the protein as well as expensive beads (e.g. Ni-NTA beads) used for binding. ITC purification is a less expensive option because it simply requires heating, cooling and centrifugation.

Figure 4:
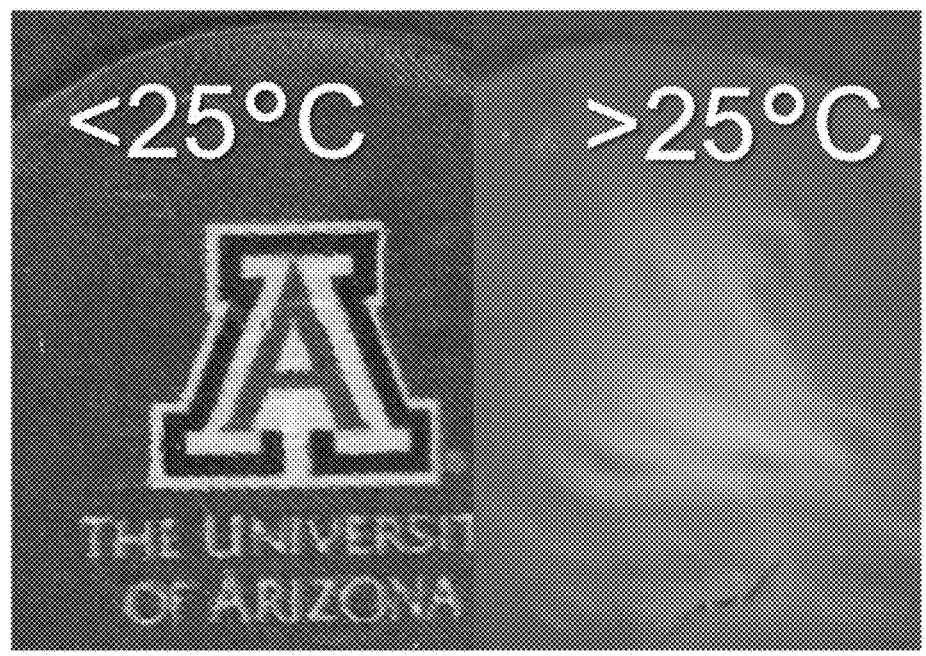
FIG. 4 shows a hydrogel made of cross-linked ELP $(A_2Y_1A_2)_{24}$ showing hydrogel thermoresponsive behavior where the hydrogel is clear below the transition temperature (e.g., below 25° C., left panel) and cloudy above the transition temperature (e.g., above 25° C., right panel).

FIG. 4 shows a hydrogel made of cross-linked ELP $(A_2Y_1A_2)_{24}$ showing hydrogel thermoresponsive behavior where the hydrogel is clear below the transition temperature (e.g., below 25° C., left panel) and cloudy above the transition temperature (e.g., above 25° C., right panel).

By genetically fusing AMP to an ELP, E. coli host expression, and ITC purification, ELP-AMP can be produced at low cost. $T_t$ behavior of the ELP may depend on environmental factors such as temperature, pH and salt concentrations.

The present invention is not limited to the aforementioned ELPs, e.g., ELP(Tyr). For example, in some embodiments, the ELP comprises ELP(DOPA) after Tyr hydroxylation by tyrosinase.

ELP-tether-AMP) is about 0.2 as described by Widder et al. in their article "*Characterization of hydration and nanophase separation during the temperature response in hydrophobic/hydrophilic elastin-like polypeptide (ELP) diblock copolymers*", published in the Soft Matter in 2017 (see Table 2).

Referring to Table 2, two protein tethers (DP>70 and $f_{tether}$: ~0.2) were introduced into the ELPs: (i) hydrophilic polymer-like unstructured protein $C_{30}$; and (ii) ELP(S)$_i$. ELP(S)$_i$=[VPGSG]$_i$; Cn=[AGAGAGPEG]$_n$ (SEQ ID NO: 5). Note i is not limited to 36 and 45, and n is not limited to 30 per Table 2.

TABLE 2

ELP(Tyr)-protein tether design with LL37

| ELP (Tyr)-tether (ELP(S)$_i$ or C$_n$) | $T_{t,\ expected}^{37}$ | m | $F_{tether}$ (Molar mass of tether/molar mass of ELP(Tyr)-tether) | $T_{t,\ experimental}$ | $T_{t,\ experimental}$ with LL37 |
|---|---|---|---|---|---|
| ELP(S$_2$Y$_1$S$_2$)$_{36}$-ELP(S)$_{36}$ | 29° C. | 180 | 0.19 | 29° C. (expected) | TBD |
| ELP(A$_2$Y$_1$A$_2$)$_{36}$-ELP(S)$_{36}$ | 26° C. | 180 | 0.20 | 26° C. (expected) | TBD |
| ELP(S$_2$Y$_1$S$_1$)$_{45}$-ELP(S)$_{45}$ | 24° C. | 180 | 0.19 | TBD | TBD |
| ELP(A$_2$Y$_1$A$_1$)$_{45}$-ELP(S)$_{45}$ | 21° C. | 180 | 0.19 | TBD | TBD |
| ELP(S$_2$Y$_1$S$_2$)$_{36}$-C$_{30}$ | >29° C. | 180 (tether not included) | 0.21 | TBD | TBD |
| ELP(A$_2$Y$_1$A$_2$)$_{36}$-C$_{30}$ | >25° C. | 180 (tether not included) | 0.22 | TBD | TBD |
| ELP(S$_2$Y$_1$S$_1$)$_{45}$-C$_{30}$ | >25° C. | 180 (tether not included) | 0.21 | TBD | TBD |
| ELP(A$_2$Y$_1$A$_1$)$_{45}$-C$_{30}$ | >20° C. | 180 (tether not included) | 0.22 | TBD | TBD |

Protein Tethers

The protein tether separates the ELP and the AMP to increase AMP activity. The protein tether is designed based on currently used synthetic polymer tethers, e.g., polyethylene glycol (PEG), with similar properties: size controlled, hydrophilic, and unstructured. The benefit of designing a protein tether is that the tether can be genetically encoded with ELP and AMP, e.g., ELP-tether-AMP is synthesized together in one polymer unit via bio-manufacturing, and purified (e.g., by ITC), which the conventional approach needs to prepare biomaterials and synthesize and purify polymer tethers and AMPs separately, and then attached end-to-end, resulting in high cost and time.

Intrinsically disordered proteins have similar flexibility to PEG due to a similar chain stiffness with a persistent length of ~0.4 nm. Hydrophilic unstructured proteins are available with precisely controllable lengths, allowing the development of the protein tether.

The tether is to be hydrophilic, unstructured, and of a certain length. For example, in certain embodiments, the tether length is at least 3000 g/mol, which is equal to a degree of polymerization (DP) of 70. In certain embodiments, for better separation between the self-assembled ELP nanoparticle and AMP, the ratio of tether size to whole biopolymer size ($f_{tether}$=molar mass of tether/molar mass of To test hydration characteristics of hydrophilic protein tethers, the hydrodynamic radius ($r_h$) of nanoparticles will be measured to observe changes of particle sizes compared to ELP(S$_2$Y$_1$S$_2$)$_{36}$ (Table 1) vs. ELP(S$_2$Y$_1$S$_1$)$_{36}$-ELP(S)$_{36}$ (Table 2), which have the same amino acid compositions but different distributions; in the absence and presence of protein tethers, the contact angle of water droplets on the AMP biopolymer films and coatings on silica will be analyzed (Table 1 and Table 2); and (iii) anti-adhesion or anti-fouling functionality will be identified via fluorescent microscopy using fluorescent-tagged bovine serum albumin on the AMP biopolymer coatings, and the result will be compared to PEG coatings. Since hydrophilic synthetic polymer PEG is well-known conventional tether with excellent anti-fouling property, the last test will help to select protein tether in Table 2 that shows promising results.

To examine plasma or serum stability of LL37 in the compositions of the present invention, samples of LL37 and ELP(Tyr)-tether-LL37 nanoparticles will be collected in 80% human plasma or serum at 37° C. in time intervals. Biomolecules in serum will be heat-inactivated right after the sample collection to prevent additional LL37 degradation, and the percentage of degradation will be analyzed by HPLC.

Antimicrobial Peptides (AMPs)

The antimicrobial peptide (AMP) may be selected from one of many known AMPs or those in future development. The present invention is not limited to the AMPs disclosed herein. A non-limiting example of an AMP is LL37, which is a cationic, amphiphilic, antimicrobial peptide, composed of 37 amino acids (LLGDFFRKSKEKIGKEFK-RIVQRIKDFLRNLVPRTES, SEQ ID NO: 6).

Regarding orientation of the AMP, AMPs tethered by their N- or C-termini may be more potent than an AMP randomly attached to tethers between its ends. AMPs that form barrel-stave pores on microbe membranes for antimicrobial activity require several AMPs in an antiparallel formation to form the pore. Several LL37 peptides form a barrel structure in an antiparallel orientation and follow the carpet or toroidal model to lyse the bacterial membrane. This covers the three most-widely accepted microbe lysis mechanisms.

The present invention features simple gene editing to encode the AMPs to be connected to a protein tether by either the N- or C-terminus for same AMP orientation (ELP-tether-AMP or AMP-tether-ELP) within the material. For AMP orientation with opposite direction in the same material, either two AMP molecules can be attached, one by the N- and one by the C-terminus (e.g., AMP-tether-ELP-tether-AMP) or by mixing two proteins (ELP-tether-LL37 and LL37-tether-ELP) in the same biomaterial, the orientation of LL37 can be alternated in the ELP-based nanoparticle, films, and adhesives.

Development of ELP(Tyr)-AMP Nanoparticle, Film, and Coating Materials

The designed $T_t$ of ELP(Tyr)-AMP facilitates ELP self-assembled nanoparticles at body temperature (BT), while Tyr residues in ELP(Tyr) can be photo-cross-linked to construct ELP(Tyr)-AMP films and hydroxylated to form ELP(DOPA)-AMP adhesives for coating biomaterial surfaces.

For example, because Tyr residues are rare in AMPs, Tyr-crosslinking using ELP(Tyr) helps to mitigate random cross-linking of AMPs and maximize AMP activity.

ELP(DOPA) may be produced by hydroxylating Tyr residues in ELP(Tyr) with commercially available mushroom tyrosinase. The ELP(DOPA)-AMP solution may be dip coated to deposit the ELP(DOPA)-AMP on biomaterial surfaces, such as alumina, Ti alloy, and polymers (e.g., ePTFE). We will monitor the dwelling time of ELP(DOPA)-AMP adhesives on surfaces in physiological buffers at BT, and the concentration of detached ELP(DOPA)-AMP proteins in solution can be determined over time using UV absorbance (280 nm) and the Beer-Lambert law.

An automated antibacterial susceptibility testing instrument can measure the minimal inhibitory concentration of free LL37 and ELP-LL37 nanoparticles against *E. coli* and *S. aureus*. The agar disk-diffusion method can be adapted to test the activity of ELP(Tyr)-LL37 films and coatings on biomaterial surfaces. For example, MacConkey agar can be prepared for *E. coli* and tryptic soy agar can be prepared for *S. aureus* to determine the LL37 activity level by measuring the zone inhibition around the film or coating material, where >1 mm is indicative of a good antibacterial agent based on Swiss Norm 195920—ASTM E 2149-01.

As previously discussed, the ELP(Tyr)-AMP films herein, using Tyr which is not found in most AMPs for cross-linking, may enhance AMP activity relative to the previously developed ELP-AMP film because AMPs were unintentionally cross-linked, resulting in a decrease in activity.

Applications

As previously discussed, the biopolymer-AMP compositions (e.g., AMP-ELP platform) have a variety of applications that include but are not limited to: antimicrobial nanoparticles as AMR therapeutics or as a pharmaceutical to treat infected individuals, antimicrobial coatings on clothing, on surfaces of implants, or on medical devices, such as endoscopes, to prevent secondary microorganism infection from the device to patient, antimicrobial filters to prevent transmission and directly kill a broad range of biological pathogens, antimicrobial films for wound dressings, etc.

Without wishing to limit the present invention to any theory or mechanism, it is believed that large-scale production and storage of AMP-ELPs may be a versatile defensive strategy against of a BWA attack or epidemic since the material can be used directly in applications ranging from a surface coating to protect personnel and infrastructure to a nanoparticle to treat BWA exposure. AMPs have shown efficacy against an extensive range of weaponizable biological pathogens such that having it on hand is invaluable preparation for an unknown or new BWA.

The present invention also provides methods for treating infections. The methods may feature the introduction of a biopolymer-AMP composition of the present invention, wherein the biopolymer-AMP composition kills the infectious agent or reduces the growth of the infectious agent.

The present invention also provides cocktails, e.g., for therapeutic purposes, wherein the cocktails comprise two or more AMP-ELPs such as ELPs with different AMPs, different ELPs with different AMPs, etc.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. An antimicrobial peptide (AMP)-biopolymer composition comprising:
   a) an elastin-like polypeptide (ELP);
   b) an antimicrobial peptide (AMP); and
   c) a hydrophilic peptide tether connecting the ELP and the AMP;
   wherein the peptide tether connects to the AMP at the AMP's N-terminus or C-terminus;
   wherein the ELP is according to the formula [(VPGXaaG (SEQ ID NO: 1))$_j$(VPGYG (SEQ ID NO: 2))$_k$ (VPGXaaG (SEQ ID NO: 1))$_l$]$_n$;
   wherein j ranges from 1-6, k ranges from 1-6, l ranges from 1-6, and n ranges from 1-50;
   wherein the Xaa comprises a single amino acid; wherein one Xaa of the formula is identical to or different from another Xaa of the formula
   wherein the AMP comprises LL37, RL37, dermcidin, or a combination thereof.

2. The composition of claim 1, wherein Xaa is alanine, serine, arginine, asparagine, aspartic acid, cysteine, glutamine, glutamic acid, glycine, histidine, isoleucine, leucine, lysine, methionine, phenylalanine, threonine, tryptophan, tyrosine, valine.

3. The composition of claim 1, wherein the protein tether comprises [VPGSG]$_i$ (SEQ ID NO: 4) or [AGAGAGPEG]$_m$ (SEQ ID NO: 5), wherein i is equal to 36 or 45 and m is equal to 30.

4. The composition of claim 1, wherein the composition self-assembles into nanoparticles.

5. The composition of claim 1, wherein tyrosine residues are cross-linked to form a self-standing film or membrane material.

6. The composition of claim 1, wherein the tyrosine residues allow the composition to adhere to a surface after hydroxylation by tyrosinase.

7. The composition of claim 6, wherein the surface is a cloth, a plastic, a glass, a metal, or a combination thereof.

8. The composition of claim 6, wherein the surface is a medical device, a dressing, a clothing, or a combination thereof.

9. The composition of claim 1, wherein the peptide tether has anti-fouling characteristics.

* * * * *